United States Patent [19]

Hauschild et al.

[11] Patent Number: 4,895,139

[45] Date of Patent: Jan. 23, 1990

[54] INFLATABLE PENILE PROSTHESIS WITH BEND RELEASE VALVE

[75] Inventors: Sidney F. Hauschild, Hendricks; Dezso K. Levius, Bloomington, both of Minn.

[73] Assignee: American Medical Systems, Inc., Minnentonka, Minn.

[21] Appl. No.: 238,008

[22] Filed: Aug. 29, 1988

[51] Int. Cl.[4] .............................................. A61F 2/26
[52] U.S. Cl. ..................................................... 128/79
[58] Field of Search ........................................... 128/79

[56] References Cited

U.S. PATENT DOCUMENTS

| | | | |
|---|---|---|---|
| 3,954,102 | 5/1976 | Buuck | 128/79 |
| 4,224,934 | 9/1980 | Scott et al. | 128/79 |
| 4,267,829 | 5/1981 | Burton et al. | 128/79 |
| 4,353,360 | 10/1982 | Finney et al. | 128/79 |
| 4,369,771 | 1/1983 | Trick | 128/79 |
| 4,383,525 | 5/1983 | Scott et al. | 128/79 |
| 4,449,520 | 5/1984 | Palomar et al. | 128/79 |
| 4,550,719 | 11/1985 | Finney et al. | 128/79 |
| 4,590,927 | 5/1986 | Porter et al. | 128/79 |
| 4,671,261 | 6/1987 | Fischell | 128/79 |
| 4,726,360 | 2/1988 | Trick et al. | 128/79 |

Primary Examiner—Gene Mancene
Assistant Examiner—Cary E. Stone
Attorney, Agent, or Firm—Peter C. Richardson; Lawrence C. Akers; Gezina Holtrust

[57] ABSTRACT

An implantable penile prosthesis comprises a tubular body for implantation in a patient's penis and a fluid reservoir for implantation in a patient's body outside the penis. The tubular body and reservoir are in fluid communication with each other. The tubular body comprises a tubular chamber which is inflatable from a flaccid to an erect state when filled substantially to capacity. Fluid flow to and from the chamber is by way of a manually actuatable valve system. The valve system moves between an open position allowing for change from the erect state to the flaccid state, and a closed position allowing for change from the flaccid state to the erect state. The valve system is movable from the second closed position to the first open position by bending of the penis.

11 Claims, 3 Drawing Sheets

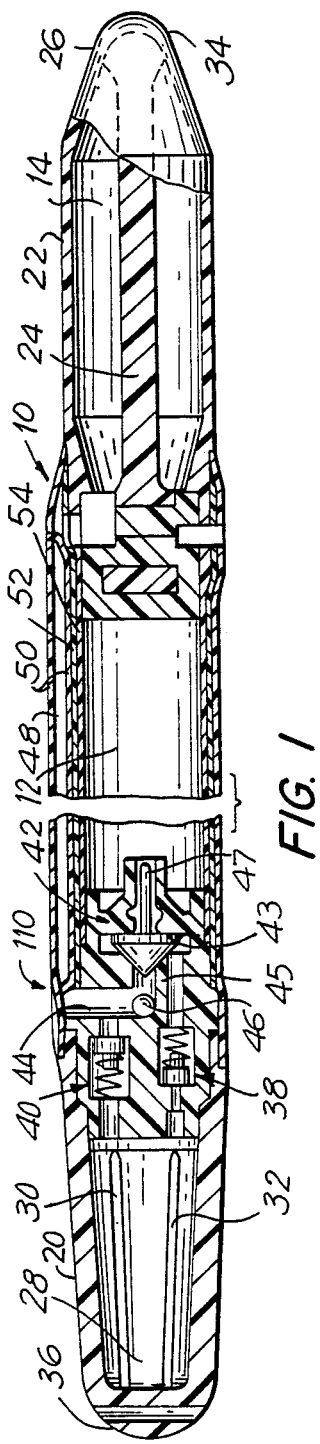
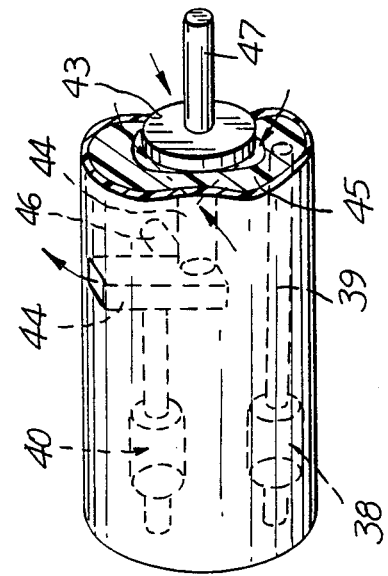
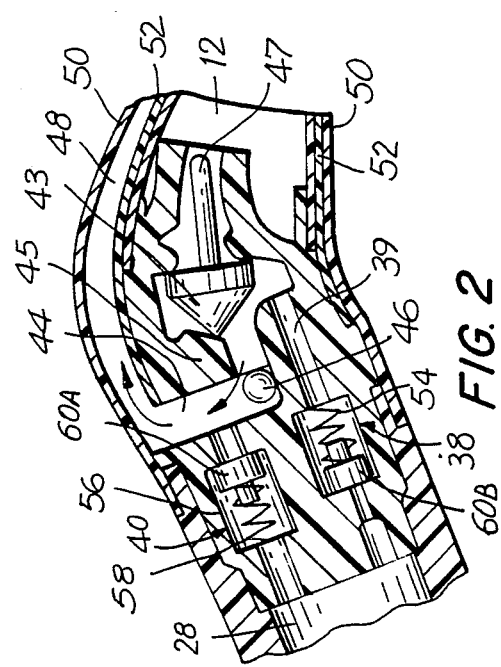

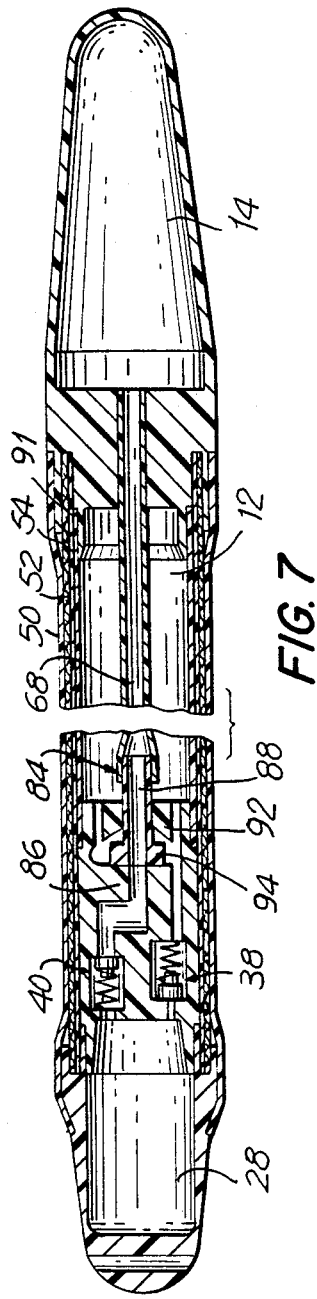
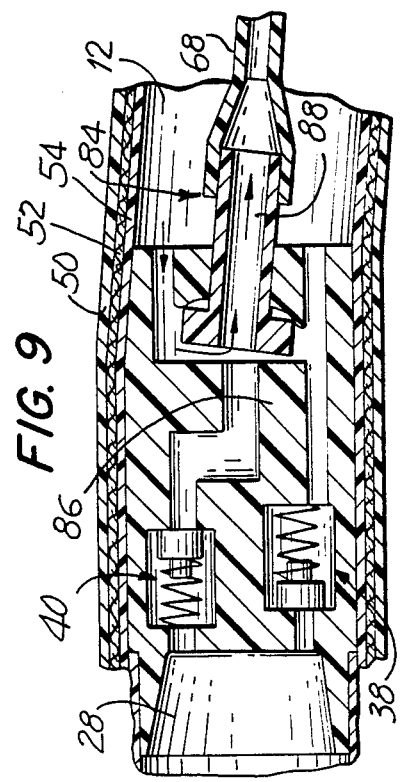
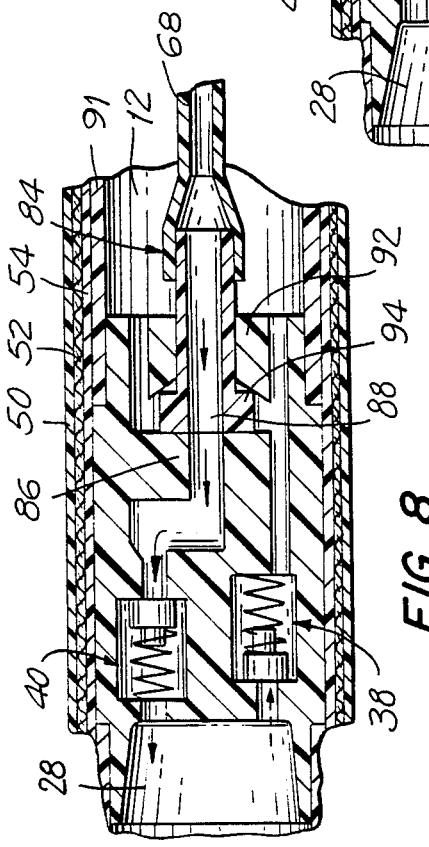
FIG. 7
FIG. 9
FIG. 8

INFLATABLE PENILE PROSTHESIS WITH BEND RELEASE VALVE

BACKGROUND OF THE INVENTION

This invention relates to an implantable unitary penile prosthesis comprising a tubular body implanted in the penis for inflation to an erect state when said body is substantially filled with a fluid substantially to capacity.

Inflatable penile devices described in the prior art generally include a tubular body for implantation in one, or usually both, of the corpus cavernosum of a patient's penis. The user produces an erection by pumping fluid to inflate the tubular body. Deflation is generally attained by manipulation of a valve system. The fluid inflatable devices require relatively large amounts of fluid to attain an erection which is sufficient to withstand the pressures and stresses during sexual intercourse. Fluid reservoirs have been implanted extraneous to the penis to accomodate the fluid requirements. U.S. Pat. No. 3,954,102 describes one such system requiring rather extensive surgery. Less invasive surgery is required with the device of U.S. Pat. No. 4,267,829 having a satellite reservoir implanted in the scrotum of a patient. Deflation of this device to the flaccid state is by manipulation of a pull valve, which is also located in the scrotum and therefore difficult to reach. U.S. Pat. No. 4,590,927 describes a self-contained device requiring limited surgery and simplified manipulation of the penis for deflation of the device. Nevertheless, simpler manipulation for deflation is desirable.

SUMMARY OF THE INVENTION

According to the invention, a unitary penile prosthesis is provided which is implantable within one or both corpus cavernosa of the penis to simulate a natural erection, said prosthesis comprising a generally tubular chamber within said penile prosthesis, inflatable from a flaccid to an erect state when filled with a fluid substantially to capacity and deflatable from the erect state to the flaccid state when substantially free of fluid, a fluid reservoir in fluid communication with said tubular chamber, and a manually actuatable valve system for controlling fluid flow between said tubular chamber and said fluid reservoir, said valve system movable between at least two different positions, a first open position allowing for change from the erect state to the flaccid state, and a second closed position allowing for change from the flaccid state to the erect state, said valve system being movable from said second closed position to said first open position by bending of the penis.

Thus, the penile prosthesis can be deflated simply by bending of the penis in any direction.

In a preferred embodiment of the invention, the valve system is operatively connected to said distal section and is movable from the first open position to the second closed position by manual compression of said distal section. Such manual compression may activate a pump located in the distal section.

In one embodiment of the invention, the valve system comprises a means for controlling fluid flow from the fluid reservoir to the tubular chamber to attain the erect state, and a first valve for controlling fluid flow from said tubular chamber to the fluid reservoir to attain the flaccid state. In a specific embodiment, the above means comprises a pump, preferably located in the distal section, and a second valve in fluid communication with the pump to allow an irreversible fluid flow from the fluid reservoir to the tubular chamber on compressing the pump.

In a further specific embodiment, the fluid reservoir is located in the proximal section, and the first and second valves are both located in the distal section. The pump and second valve conveniently are in fluid communication through a first passageway which is in fluid isolation from the tubular chamber, whereas the tubular chamber is in fluid communication with the fluid reservoir through a second passageway which is in fluid isolation from the tubular chamber.

The above first passageway may be defined by a conduit extending axially along the length of the tubular body externally of the tubular chamber. The above second passageway may be defined by a conduit extending axially along the length of the tubular body in fluid isolation from the first passageway.

BRIEF DESCRIPTION OF THE DRAWINGS

FIG. 1 is a cross-sectional view of a prosthesis according to the invention in its erect state.

FIG. 2 is a cross-sectional view of the valve system of FIG. 1.

FIG. 3 is a perspective view of the valve system of FIG. 1 taken along line 3—3 of FIG. 1.

FIG. 7 is a cross-sectional view of a prosthesis according to the invention in its erect state.

FIG. 8 is a cross-sectional view of the valve system of FIG. 7 in the pumping position.

FIG. 9 is a cross-sectional view of the valve system of FIG. 7 in the release position.

DETAILED DESCRIPTION OF THE INVENTION

Figure 4:
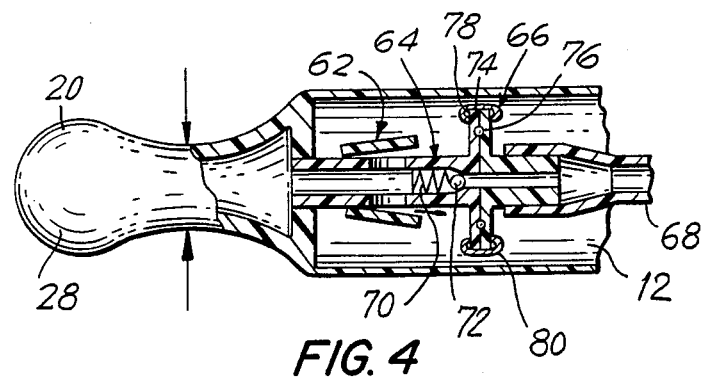
FIG. 4 is a cross-sectional view of a valve system according to the invention in the pressure phase of the pumping cycle.

Like references are used for like parts throughout the description of the drawings.

FIG. 1 shows penile prosthesis 10 of the present invention comprising a generally tubular chamber 12 and fluid reservoir 14. Penile prosthesis 10 is implanted within each of the two corpus cavernosa of the penis, although one penile prosthesis 10 may be implanted in either corpus cavernosum and still achieve useful results.

All of the components of prosthesis 10 are either composed of or covered by a biocompatible material such as silicone.

Penile prosthesis 10 has distal section 20 and proximal section 22. Proximal section 22 is usually positioned in the rear of the corpus cavernosum under the puboischiatic rami. Proximal section 22 defines the fluid reservoir 14. A rigid stabilizer 24 extends rearwardly from the end of the tubular chamber 12 centrally through the fluid reservoir 14 to the rear tip 26. The stabilizer 24 serves to maintain the shape of the rear fluid reservoir 14 and provide rigidity regardless of the amount of fluid contained therein. A conventional rear tip extender (not shown) may be provided to lengthen prosthesis 10, if needed, to lessen the need for different prosthesis sizes.

The distal section 20 contains pump 28 which is manually actuatable for inflation of tubular chamber 12 which is located in series with respect to pump 28. The pump 28 is advantageously a hollow circular chamber. The pump 28 supplies fluid pressure by lateral squeezing of distal section 20. The ribs 30 and 32 extend from the distal end of the valve system 34 to the front tip 36. The ribs 30 and 32 serve the same purpose as stabilizer 24 in the fluid reservoir 14. The front tip 36 is advantageously substantially rigid to resist buckling during intercourse.

The tubular chamber 12 is positioned within prosthesis 10 such that on implantation of prosthesis 10, the tubular chamber 12 lies approximately medially along the length of the corpus cavernosum.

The manually actuatable valve system for controlling fluid flow between the tubular chamber 12 and the fluid reservoir 14 comprises pump 28, pressure valve 38, suction valve 40, and release valve 42. The valve system in FIG. 1 is in the second closed position. Pump 28 is in fluid communication with pressure valve 38 and suction valve 40 to allow an irreversible fluid flow from fluid reservoir 14 to tubular chamber 12 on compressing and releasing the pump 28. Valves 38 and 40 are located in distal section 20 in series with the tubular chamber 12 along the length of the prosthesis 10.

The release valve 42 includes cone 43 and valve block 45. The tubular chamber 12 communicates with the fluid reservoir 14 when pressure is applied to the valve stem 47 so deforming valve block 45 which is made of a material such as rubber. When the cone 43 is sealed against the valve block 45, fluid can flow from the fluid reservoir 14 to the pump 28.

The suction valve 40 communicates at its proximal end with a radially oriented passageway 44 which in turn communicates with a transverse, radially oriented passageway 46 which is generally perpendicular to passageway 44. The passageway 44 communicates with an axial, lengthwise passageway 48. The passageway or conduit 48 extends from the distal portion 20 to the proximal portion 22 in fluid isolation from the tubular chamber 12.

The fluid of use in the prosthesis is a biocompatible fluid such as a physiological saline solution or a radio-opaque fluid.

The tubular chamber 12 has three different layers 50, 52 and 54. The outer layer 50 and the inner layer 54 are formed of any material which is elastic such as silicone elastomer. Materials which may be used for the three layers are disclosed in above U.S. Pat. No. 4,267,829. The middle layer 52, for instance, is made of a substantially non-distensible material such as a vascular graft material of Dacron ® polyester fibers. The three layers may be replaced by one layer having the desirable properties of non-distensibility and imperviousness to liquids.

The pressure valve 38 and the suction valve 40 are as described in above U.S. Pat. No. 4,590,927. Referring to FIGS. 2 and 3, both valves include a housing 56, a coiled spring 58 and a valve member 60. The coiled spring 58 biases the valve member 60A of valve 40 proximally and the coiled spring 54 of valve 38 biases the valve member 60B distally.

Figure 5:
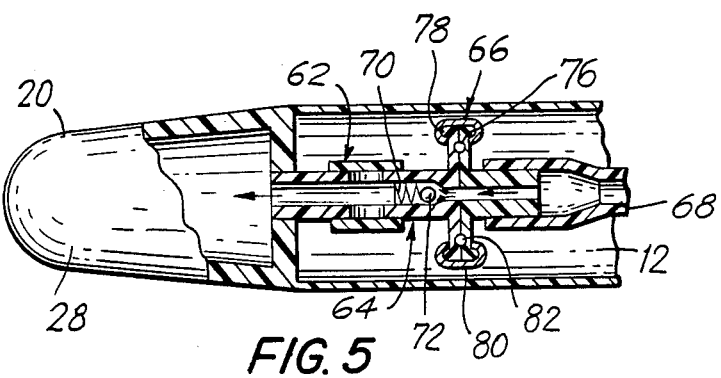
FIG. 5 is a cross-sectional view of the valve system of FIG. 4 in the draw phase of the pumping cycle.
Figure 6:
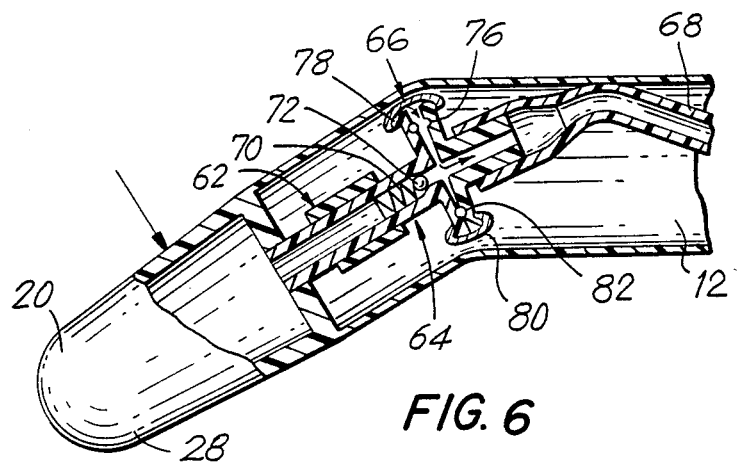
FIG. 6 is a cross-sectional view of the valve system of FIG. 4 in the first open or release position.

In FIGS. 4 to 6, the valve system comprises the pump 28, the flap valve 62, the poppet valve 64, and the double flange valve 66. Pump 28 communicates with fluid reservoir 14 through lumen 68, shown partially. The three valves 62, 64 and 66 are positioned within tubular chamber 12, shown partially. Poppet valve 64 has a coil spring 70 which biases poppet 72 proximally. The poppet 72 seals against opening 74 when the coil spring 70 is extended. The double flange valve 66 includes two flanges 76 and 78 which are held together by several spring retainers 80. O-ring seal 82 between flanges 76 and 78 seals the two flanges 76 and 78 to prevent fluid flow between the two flanges when the double flange valve 66 is closed.

The tubular chamber 12 partially shown in FIGS. 4 to 6 generally has four different layers, as described below with reference to FIG. 7.

FIGS. 7 to 9 show a valve system comprising pump 28, pressure valve 38, suction valve 40, and bend valve 84. The pump 28 and the valves 38 and 40 are as described above with reference to FIGS. 1 to 3. Tubular chamber 12 is generally made of the three different layers 50, 52 and 54 described above. In addition, there is an inner tube 91 made of a wear-resistant material such as polytetrafluoroethylene. The three layers 50, 52 and 54 may be replaced by one layer.

The pump 28 communicates with the fluid reservoir 14 through the suction valve 40, the bend valve 84 and lumen 68. The bend valve 84 includes a valve block 86 and a valve channel 88 which aligns with valve block passage 90 in FIGS. 7 and 8. The valve channel 88 has a valve channel extension 94 which rests against a channel support block 92 in FIG. 9. The support block 92 is made of a material such as rubber that is compressible by the extension 94 on bending the valve channel 88 relative to the valve block 86.

OPERATION

The tubular chamber 12, the pump 28, and the fluid reservoir 14 are supplied with biocompatible fluid by means known to those skilled in the art. Prosthesis 10 is then implanted by surgical means known in the art. Once implanted, when an erection of the penis is to be produced, the user squeezes the distal section 20. On repeated squeezing and releasing of the distal section, fluid fills the tubular chamber 12 substantially to capacity and the desired stiffness and girth of prosthesis 10, and the penis, is attained.

Referring to FIGS. 1 to 3, on squeezing distal section 20, fluid transfers from pump 28 through pressure valve 38, which opens due to the fluid pressure, and valve channel 39 to tubular chamber 12. The user then releases distal section 20, creating a vacuum in pump 28, so opening suction valve 40, and drawing fluid from fluid reservoir 14 through passageway 48 into pump 28.

The user deflates the prosthesis 10 by bending the penis at valve stem 47 as shown in FIG. 2, or by laterally squeezing prosthesis 10 at the valve block 45 as shown in FIG. 3. The bending or squeezing forces deform valve block 45 and allow fluid to flow from tubular chamber 12 past cone 43 through passageways 44 and 48 to fluid reservoir 14 (not shown) until the penis is flaccid. Alternatively or simultaneously, fluid flows from tubular chamber 12 past cone 43 through passageway 46 between outer layer 50 and middle layer 52 to passageway 48. The direction of the fluid is indicated by arrows in FIGS. 2 and 3.

Referring to FIGS. 4 to 6 in conjunction with FIG. 7, on squeezing distal section 20, fluid transfers from pump 28 through flap valve 62 into tubular chamber 12, as indicated by arrows in FIG. 4, showing the valve system in the second closed position. The poppet valve 64 and the double flange valve 66 are closed preventing fluid flow through lumen 68 to fluid reservoir 14. The user then releases distal section 20 creating a low pressure in pump 28 so opening poppet valve 64 and closing flap valve 62, and drawing fluid from fluid reservoir 14 through lumen 68 into pump 28, as indicated by arrows in FIG. 5 showing the valve system in the second closed position of the valve system during the draw phase of the pumping cycle. The user deflates the prosthesis 10 by supporting the penis at a position proximal to double flange valve 66 and by bending distal section 20 such that spring retainers 80 are in a flexed position, and valve 66 opens. The user's action forces the fluid under pressure in tubular chamber 12 to pass through open valve 66 and lumen 68 to the reservoir 14 until the penis is flaccid. The arrows in FIG. 6 indicate the flow of fluid during the bending action.

Referring to FIGS. 7 to 9, on squeezing distal section 20, fluid transfers from pump 28 through pressure valve 38 to tubular chamber 12, as shown by broken arrows (→) in FIG. 8 showing the valve system in the second closed position during the pumping phase of the pumping cycle. The user then releases distal section 20, creating a low pressure in pump 28 so opening suction valve 40, and drawing fluid from fluid reservoir 14 through central lumen 68, bend valve 84 and suction valve 40 into pump 28, as indicated by solid arrows in FIG. 8. The user deflates the prosthesis 10 by bending the penis such that bend valve 84 is at an angle relative to valve block 86. The bending action forces the fluid under pressure in tubular chamber 12 to pass between valve block 86 and bend valve 84 through central lumen 68 to fluid reservoir 14 until the penis is flaccid. The arrows in FIG. 9 show the flow of fluid during bending when the valve system is in the first open position.

The invention has been described with respect to three embodiments. Those skilled in the art will appreciate variations and modifications thereof. The following claims are intended to cover all modifications and variations falling within the spirit and scope of the invention.

We claim:

1. A unitary penile prosthesis implantable within one or both corpus cavernosa of the penis to simulate a natural erection comprising:
   a generally tubular chamber within said penile prosthesis, inflatable from a flaccid to an erect state when filled with a fluid substantially to capacity and deflatable from the erect state to the flaccid state when substantially free of fluid,
   a fluid reservoir in fluid communication with said tubular chamber, and
   a manually actuatable valve system for controlling fluid flow between said tubular chamber and said fluid reservoir, said valve system movable between at least two different positions, a first open position allowing for change from the erect state to the flaccid state, and a second closed position allowing for change from the flaccid state to the erect state, said valve system being movable from said second closed position to said first open position by bending of the penis.

2. A prosthesis according to claim 1 wherein said penile prosthesis has a proximal section and a distal section, said valve system is operatively connected to said distal section, and said valve system is movable from the first open position to the second closed position by manual compression of said distal section.

3. A prosthesis according to claim 2 wherein said valve system comprises a pump located in said distal section.

4. A prosthesis according to claim 1 wherein said valve system comprises a means for controlling fluid flow from said fluid reservoir to said tubular chamber to attain the erect state, and a first valve for controlling fluid flow from said tubular chamber to said fluid reservoir to attain the flaccid state.

5. A prosthesis according to claim 4 wherein said means comprises a pump and a second valve, said second valve being in fluid communication with said pump to allow an irreversible fluid flow from said fluid reservoir to said tubular chamber on compressing said pump.

6. A prosthesis according to claim 5 wherein said fluid reservoir is located in said proximal section.

7. A prosthesis according to claim 6 wherein said first valve and said second valve are both located in said distal section.

8. A prosthesis according to claim 7 wherein said pump and said second valve are in fluid communication through a first passageway which is in fluid isolation from said tubular chamber.

9. A prosthesis according to claim 8 wherein said tubular chamber is in fluid communication with said fluid reservoir through a second passageway which is in fluid isolation from said tubular chamber.

10. A prosthesis according to claim 8 wherein said first passageway is defined by a conduit extending axially along the length of said tubular body externally of said tubular chamber.

11. A prosthesis according to claim 9 wherein said second passageway is defined by a conduit extending axially along the length of said tubular body in fluid isolation from said first passageway.

* * * * *